United States Patent
Igler (10) Patent No.: US 10,492,752 B2
(45) Date of Patent: Dec. 3, 2019

(54) METHOD AND MEDICAL APPARATUS FOR AUTOMATICALLY POSITIONING A PATIENT

(71) Applicant: Siemens Healthcare GmbH, Erlangen (DE)

(72) Inventor: Harald Igler, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/118,626

(22) Filed: Aug. 31, 2018

(65) Prior Publication Data

US 2019/0069870 A1    Mar. 7, 2019

(30) Foreign Application Priority Data

Sep. 4, 2017   (EP) ..................................... 17189185

(51) Int. Cl.
| | |
|---|---|
| *A61B 6/00* | (2006.01) |
| *G01V 8/20* | (2006.01) |
| *G01R 33/30* | (2006.01) |
| *A61B 6/04* | (2006.01) |
| *A61B 5/055* | (2006.01) |

(Continued)

(52) U.S. Cl.
CPC ............ *A61B 6/547* (2013.01); *A61B 5/0555* (2013.01); *A61B 6/0407* (2013.01);
(Continued)

(58) Field of Classification Search
CPC ..... A61B 5/0555; A61B 6/032; A61B 6/0407; A61B 6/0457; A61B 6/0492; A61B 6/08;
(Continued)

(56) References Cited

U.S. PATENT DOCUMENTS

| | | |
|---|---|---|
| 8,378,325 B2 | 2/2013 | Fadler |
| 8,712,501 B2 | 4/2014 | Ritter |

(Continued)

FOREIGN PATENT DOCUMENTS

| | | |
|---|---|---|
| DE | 10 2006 052711 A1 | 5/2008 |
| DE | 10 2008 013 613 A1 | 9/2009 |

(Continued)

OTHER PUBLICATIONS

"Directive 2013//35/EU of teh European Parliament and of the Council on the Minimum Health and Safety Requirements Regarding the Exposure of Workers to the Risks Arising from Physical Agents (Electromagnetic Fields)," (corrected version) (2015).

(Continued)

*Primary Examiner* — Michael T Rozanski
(74) *Attorney, Agent, or Firm* — Schiff Hardin LLP (57) ABSTRACT

In a method and apparatus for automatic positioning of a patient relative to a medical device, the patient is positioned on a patient support of the medical device in a detection area of an optical position determining device of the medical device. The optical position determining device has at least one three-dimensional light curtain arrangement. A start position of the patient is detected by the optical position determining device and a position deviation between the start position detected and a target position stored in a control processor is determined. Depending on the position deviation, the patient support is automatically positioned in three dimensions.

12 Claims, 3 Drawing Sheets

(51) Int. Cl.
*A61B 6/03* (2006.01)
*A61B 6/08* (2006.01)
*A61N 5/10* (2006.01)

(52) U.S. Cl.
CPC .......... *A61B 6/0457* (2013.01); *A61B 6/0492* (2013.01); *A61B 6/545* (2013.01); *G01R 33/307* (2013.01); *G01V 8/20* (2013.01); *A61B 6/032* (2013.01); *A61B 6/08* (2013.01); *A61N 5/1049* (2013.01)

(58) Field of Classification Search
CPC ...... A61B 6/545; A61B 6/547; A61N 5/1049; G01R 33/307; G01V 8/20
See application file for complete search history.

(56) References Cited

U.S. PATENT DOCUMENTS

| | | |
|---|---|---|
| 2008/0108892 A1 | 5/2008 | Ritter |
| 2011/0006230 A1 | 1/2011 | Fadler |
| 2013/0279779 A1 | 10/2013 | Darrow et al. |
| 2014/0210468 A1 | 7/2014 | Xu |
| 2014/0233041 A1 | 8/2014 | Reitz et al. |

FOREIGN PATENT DOCUMENTS

| | | |
|---|---|---|
| DE | 10 2009 032431 A1 | 1/2011 |
| DE | 10 2014 219 666 A1 | 3/2016 |

OTHER PUBLICATIONS

"3-D Coordinate Measuring Technology in a Table-Top Device,," Keyence Corp.(2017).
Bonnow, "Image-Guided 3-D Corrdinate Measuring Machine from Keyence in Use at Eduard Kronenberg," Keyence Corp. (2017).
"Ordinance on the Protection of Employees Against Risks from Electromagnetic Fields (EMFV)," European Union (2016).
European Search Report dated Feb. 23, 2018, and English language translation.
German Application No. 17 189 185.6, Intent to grant dated May 9, 2019, and English language translation.

METHOD AND MEDICAL APPARATUS FOR AUTOMATICALLY POSITIONING A PATIENT

BACKGROUND OF THE INVENTION

Field of the Invention

The invention concerns a method for automatically positioning a patient relative to a medical apparatus, as well as a medical apparatus, and a non-transitory, computer-readable data storage medium designed to implement such a method.

Description of the Prior Art

For many examinations or treatments of a patient, extremely accurate positioning of the patient is necessary in order to enable the corresponding imaging or treatment to be carried out with the desired precision. In order to allow efficient positioning of the patient and to ensure that medical staff are protected from electromagnetic radiation that may be emitted by medical devices, it is desirable if such positioning can be carried out automatically and requires no manual intervention by operating personnel. Various methods for automatic positioning of patients are known.

DE 10 2014 219 666 A1 describes a method for automatic patient positioning wherein a 3D image of a patient positioned on patient table is used, the image having been taken by a 3D camera and containing depth information. A first region of interest having a first start position and a first end position is selected via screen-displayed image information of the 3D image. A first position of the first region of interest relative to a scanner is determined on the basis of the depth information and on the selection of the first region of interest. The first region of interest is then automatically positioned in the first position by moving the patient table relative to the scanner.

SUMMARY OF THE INVENTION

An object of the invention is to provide an improved method for automatic positioning of a patient.

For a method of the type described above according to the invention the patient is positioned on a patient support of the medical apparatus within a detection area of an optical position determining device of the medical apparatus. The said optical position determining device has at least one three-dimensional light curtain arrangement, wherein a start position of the patient is ascertained by the optical position determining device and a position deviation between the ascertained start position and a target position stored in a control processor is determined. The patient support is automatically positioned in the target position in up to three dimensions based on the position deviation.

The advantage of the method according to the invention is that a start position can be acquired in three dimensions by positioning the patient on the patient support, e.g. a patient table, in the detection area of the optical position determining device that has at least one three-dimensional light curtain arrangement. This allows it to be determined, for example, how a patient is lying on the support, i.e. how he/she is oriented and positioned on the tabletop of the patient table. The start position of the patient is ascertained by the optical position determining device once the patient has assumed a position on the patient support. A position deviation is determined between this start position and the target position stored in the control processor. This position deviation describes magnitude of the deviation between the start position and the target position in all three dimensions. This deviation is ascertained by the control processor for each dimension.

Based on this position deviation, the patient support is then automatically positioned in up to three dimensions, e.g. in a longitudinal direction and/or a transverse direction and/or a vertical direction. As a result, the patient position of the patient on the patient support is changed from the start position so that it coincides with the target position as precisely as possible. The start position, i.e. the patient position, can relate to the position of a patient's specific body part to be examined or treated by the medical device, and usually also includes, as mentioned, the orientation of the patient. Another advantage of the invention is that, because of the automatic positioning of the patient support, the patient can assume a position on the patient support that need not be the same position needed for the examination or treatment, thereby obviating the need for manual positioning of the patient by medical staff.

The patient support can be automatically positioned, for example, by actuators such as electric motors or hydraulic actuators. Positioning of the patient support in three dimensions provides at least three translational degrees of freedom of the patient support. In addition, three rotational degrees of freedom can be provided in the positioning of the patient support so that a rotational movement of the patient is possible in addition to a translational movement of the patient. The control processor can be an external control device that is connected to the medical device, or a control device that is part of the medical device can be used.

In an embodiment of the invention, a three-dimensional light curtain arrangement is used that has, or produces, a number of light curtains having respective detection areas that intersect, at least partially, at an angle. As used herein, a light curtain arrangement means an arrangement of a number of light barriers that are typically disposed in at least one plane. An object placed in this plane, and that is wider in a direction orthogonal to the propagation direction of the light of the light barriers than the distance of the individual light barriers from one another can be detected by the light curtain when that object is in the detection area thereof. The object placed in the detection area of the light curtain breaks one or more light barriers, thereby enabling its position in the at least one plane of the light curtain to be determined. In the case of a three-dimensional light curtain arrangement having a number of light curtains whose detection areas at least partially intersect at an angle, the position of the object can be determined in three dimensions in a corresponding manner.

In an embodiment, the light curtain arrangement can produce at least one light curtain that has a two-dimensional detection area formed by light barriers disposed in a number of planes, e.g. parallel planes. In a preferred case it is sufficient for three-dimensional position determination if two light curtains having such a two-dimensional detection area are disposed such that at least some of their detection areas intersect at an angle, so that an overall three-dimensional detection area of the light curtain arrangement is produced in the overlap region of the two-dimensional detection areas of the light curtains.

In a preferred embodiment of the invention, a first light curtain having a detection area disposed essentially parallel to a surface of the patient support for patient positioning, and a second light curtain having a detection area disposed at an angle with respect to that patient support surface positioning, are used. The first light curtain each and/or the second light curtain each have, for example, a two-dimensional detection area so that the position of the patient positioned on the patient support can be determined in three dimensions. The patient support surface for patient positioning can be, e.g., the tabletop of a patient table, or the seat of a patient chair. A first light curtain and a second light curtain having detection areas of different size or different shape can be used, depending on the design of the patient support.

In another preferred embodiment of the invention, the second light curtain at least partially penetrates a patient-receiving aperture of the medical device. The patient-receiving aperture can be an opening of the medical device, e.g. the bore of an MRI scanner or the gantry of a CT scanner, into which the patient, or rather the patient support on which the patient is positioned, can be moved. The second light curtain is disposed such that it at least partially penetrates the patient-receiving aperture. This enables the position of the patient to be determined by the light curtain even within the patient-receiving aperture. The detection area of the second light curtain is thus at least partially inside the patient-receiving aperture. It is possible for the second light curtain to be disposed such that, in addition to part of the interior of the patient-receiving aperture, the detection area also includes an area outside, preferably in front of, the patient-receiving aperture so that a start position of a patient who has not yet been moved into the patient-receiving aperture, e.g. in the case the patient disposed on a patient support which is located in front of the patient-receiving aperture, can be detected by the second light curtain.

According to the invention, during imaging and/or treatment to be carried out by the medical device, after the first automatic positioning of the patient support the instantaneous position of the patient is continuously determined by the optical position determining device. This means that even for a patient who has already been moved to the target position, an instantaneous position of the patient describing a patient position at a given moment is continuously determined by the optical position determining device. This requires that the target position of the patient is in the detection area of the optical position determining device. If, during imaging and/or treatment to be carried out by the medical device, there is found to be a deviation between the instantaneous position of the patient and the target position, this can produce, for example, an audible or visual notification to the patient and/or an operator if a first limit value of the position deviation is exceeded, requesting him/her to return to the target position. It is also possible for a position deviation between the instantaneous position of the patient and the target position exceeding a first limit value or exceeding a second limit value to result in the imaging and/or treatment being aborted. The notification, which preferably includes a specific self-positioning instruction to the patient, is preferably given in situations in which the patient position cannot be moved to the target position by automatic positioning of the patient support. This can occur, for example, because the position deviation is too large to be compensated by positioning of the patient support.

In a further embodiment, the patient support is automatically re-positioned in the event of a position deviation occurring during imaging and/or treatment between the instantaneous position of the patient and the at least one target position stored in the control processor. This advantageously allows automatic tracking of the patient during imaging and/or treatment, and enables position deviations between the patient position and the target position that are caused, e.g., by movements of the patient to be compensated.

According to the invention, the target position is determined by the control processor on the basis of process information describing imaging and/or treatment to be carried out by the medical device, and is stored in the control processor. The target position thus can be determined on the basis of parameters such as, for example, the position of an isocenter of the imaging and/or treatment to be carried out. Consequently, different target positions can be determined for different imagings and/or treatments and stored in the control processor. This enables the patient to be positioned according to the imaging and/or treatment to be carried out, wherein the type of imaging and/or treatment to be carried out can be communicated to the control processor, such as, by operating personnel, via a user interface or a communications link.

In a preferred embodiment of the invention, a number of target positions are stored in the control processor, which are used at different times during imaging and/or treatment to be carried out by the medical device for a positioning sequence having a number of automatic positionings of the patient support. This enables the support to be moved to a number of target positions at different times during imaging and/or treatment, by automatic positioning of the patient support, so that imaging of different regions of the patient and/or in different depths or similar can be performed. For moving to a particular target position, both the start position, taking into account all the positionings already performed, can be used. Alternatively, in the case of a possibly determined instantaneous position of the patient, the latter can be employed. However, the position sequence can also describe a movement path of the patient if a deliberate movement is to take place during the imaging and/or treatment.

According to the invention, at least one accessory unit assigned to the medical device is provided, in particular a sensor. The position of the accessory unit is determined by a position determining processor and the target position is determined by the control processor depending on the accessory unit position. The automatic positioning of the patient therefore takes place taking into account the accessory unit position of at least one accessory unit, wherein different types of target position dependencies can be provided for different accessory units. The position determining processor can be part of the medical device or part of the accessory unit assigned to the medical device. In the latter case, communication of the accessory unit position to the medical device and/or the control device can be provided. For example, the position determining processor of the accessory unit can be designed to carry out a triangular time interval measurement, e.g. by analyzing phase differences of pulsed light signals, and to transmit the determined accessory unit position to the medical device and/or the control processor.

In a preferred embodiment of the invention, the position determining processor of the accessory unit can make use of at least one photosensor and/or a photoreceiver for position determination. The accessory unit position can be determined by the optical position determining arrangement of the medical device implemented as the three-dimensional light curtain arrangement. The accessory unit can have a photosensor and/or a photoreceiver, for example, wherein light transmitted from the accessory unit can be detected by the three-dimensional light curtain arrangement or wherein light transmitted by the three-dimensional light curtain arrangement can be received by the accessory unit. This provides a simple way of also determining the accessory unit position in addition to the patient position.

Also according to the invention, during the imaging and/or treatment to be carried out by the medical device, at least one updated target position is determined depending on the accessory unit position of the at least one accessory unit and is stored in the control processor. In the event of a position deviation between the instantaneous position of the patient and the at least one updated target position, the patient support is automatically re-positioned. If the position of the accessory unit changes, e.g. if an accessory unit disposed on the patient slips out of place due to a movement of the patient, an updated target position can be provided in accordance with the changed accessory unit position. If the updated target position determined is at variance with the instantaneous position of the patient, the instantaneous position of the patient can be changed by automatic re-positioning of the patient support. This enables the patient to be tracked according to the accessory unit position. Position deviation between the accessory unit position and the instantaneous position of the patient can be additionally or alternatively determined. In the event of a position deviation that exceeds a predefined limit value beyond which it is inadvisable to continue the imaging and/or treatment, the patient can be given a visual or audible notification designed to cause the patient to change his/her position and/or the position of the accessory unit, such that the imaging and/or treatment can be meaningfully continued. A separate limit value assigned to the accessory unit can be used, or one or more limit values can be used for the accessory unit that correspond to the first limit value and/or the second limit value of the deviation of the instantaneous position of the patient from the target position. A notification, which can preferably include a specific self-positioning instruction to the patient, is preferably issued in situations in which the patient position cannot be moved to the target position by automatic positioning of the patient support e.g. because the position deviation is too large to be compensated by positioning of the patient support. In addition or alternatively, the imaging and/or treatment can be aborted in this case. It is preferable, however, if, because of the movement options provided by the patient support, the target position can be correctly assumed in order to automatically re-position the patient correctly.

In another embodiment of the invention, for each automatic positioning of the patient support, positioning information describing this positioning and/or the instantaneous position of the patient and/or the target position is stored in the control processor. Consequently, the one or more items of positioning information make it possible for the positioning of the patient support to be used for documentation and/or reproducibility of the scan. Said positioning information can also describe the patient's instantaneous position on which the automatic positioning is based, and/or the target position on which the automatic positioning is based, thus allowing precise documentation of the automatic positioning of the patient during imaging and/or treatment. It is also possible for the positioning information to contain supplementary data relating to the imaging and/or treatment carried out and/or relating to operating parameters of the medical device, so that the entire process can be reproduced and used to evaluate imaging and/or treatment.

A medical device according to the invention is designed to carry out the method according to the invention as described above. All features and embodiments relating to the method apply accordingly to the medical device.

The present invention also encompasses a non-transitory, computer-readable data storage medium encoded with programming instructions (program code) that, when the storage medium is loaded into a computer or computer system of a medical apparatus, cause the computer or computer system to operate the medical apparatus so as to implement any or all embodiments of the method according to the invention, as described above.

DESCRIPTION OF THE PREFERRED EMBODIMENTS

Figure 1:
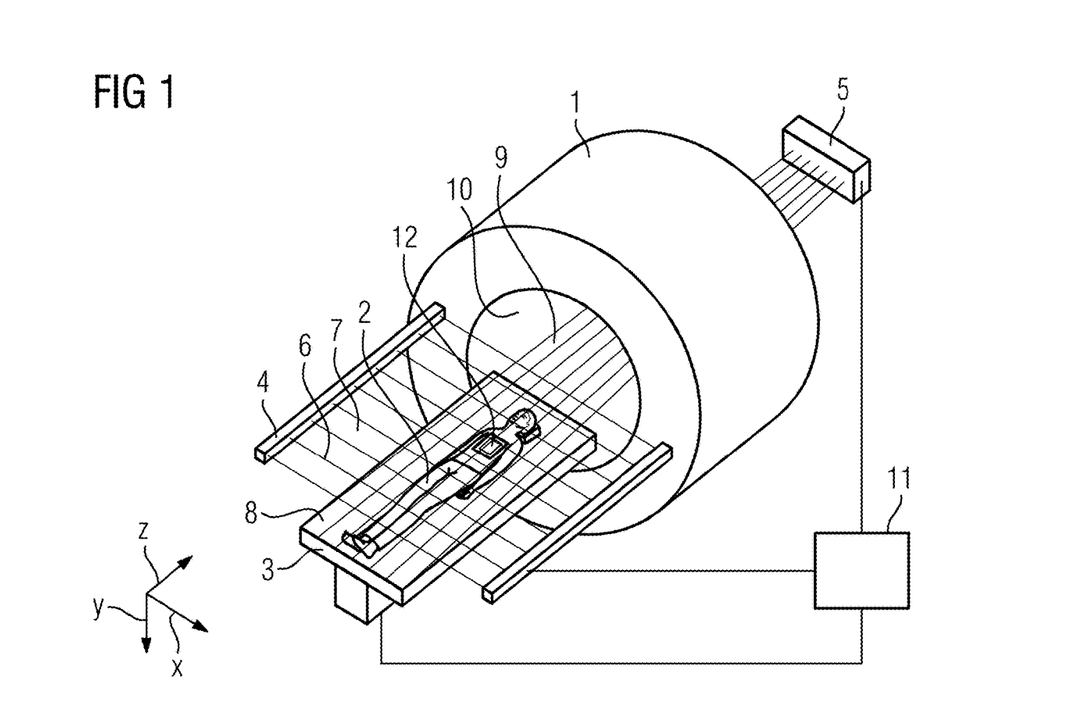
FIG. 1 is a schematic perspective illustration of a medical device according to the invention.

FIG. 1 is a schematic perspective illustration of a medical device 1 according to the invention. For automatic positioning of a patient 2, it has a patient support in the form of a patient table 3, which can be moved in three dimensions by actuators such as, for example, electric motors and/or hydraulic actuators (not shown). The medical device 1 also has a three-dimensional light curtain arrangement as an optical position determining device, wherein the three-dimensional light curtain arrangement has a first light curtain 4 and a second light curtain 5.

The first light curtain 4 has an arrangement of light barriers 6 forming a detection area 7 that runs essentially parallel to a surface 8 of the patient table 3. For clarity, only one plane of the detection area 7 is shown, but the first light curtain 4 comprises other light barriers 6 that are disposed such that the detection area 7 is extended in the y-direction by a number of planes disposed parallel to one another.

The detection area 9 of the second light curtain 5 partially penetrates a patient-receiving aperture 10 of the medical device 1 and is disposed at an angle with respect to the surface 8 of the patient table 3. In order to enable the light emitted by the second light curtain 5 to be detected, it can be provided that the surface 8 of the patient table 3 is reflecting to that the light emitted by the second light curtain 5 is sent back to the light curtain 5. Additionally or alternatively, the surface 8 of the patient table 3 has photosensors for detecting the light of the second light curtain 5 incident on the surface 8. It can also be provided for the light curtain 5 that the detection area 9 includes a number of planes, e.g. such that the entire surface 8 of the patient table 3 is covered by the detection area 9 of the second light curtain 9.

The three-dimensional light curtain arrangement formed by the first light curtain 4 and the second light curtain 5 allows three-dimensional determination of a patient position of the patient 2.

A start position of the patient 2, as shown as an example in FIG. 1, can be determined by the three-dimensional light curtain arrangement and communicated to a control processor 11. The control processor 11 can be part of the medical device 1, or it can be an external control device, e.g. a computer, connected to the medical device 1. The control processor 11 determines a position deviation between the start position of the patient and a target position stored in the control processor 11. Depending on this position deviation, automatic positioning of the patient support in three dimensions can then take place by control of the actuators of the patient table by the control processor 11, thereby enabling the patient 2 to be placed in the target position.

The automatic positioning of the patient table and therefore of the patient 2 can include, for example, moving the patient table 3 in the z-direction, i.e. into the bore 10 of the medical device 1, and/or positioning the patient table 3 in the x-direction and/or in the y-direction. A patient position such as, for example, the position of a body part or of a region of the patient that is the target of the imaging and/or treatment to be carried out by the medical device 1 is used as the start position of the patient. The target position stored in the control processor 11 can be determined according to the imaging and/or treatment to be carried out by the medical device 1 so that, for example, an isocenter of the medical device 1 in relation to the imaging and/or treatment to be carried out can be used as the target position.

The medical device 1 can be assigned an accessory unit 12, the accessory unit position of which can be determined by a position determining processor. In the embodiment shown in FIG. 1, the position determining processor can include one or more photoreceivers and/or photosensors (not shown) of the accessory unit 12, which enable the position of the accessory unit to be determined by the three-dimensional light curtain arrangement of the medical device 1.

The target position stored in the control processor 11 can be determined according to the accessory unit positions of the accessory unit 12.

Figure 2:
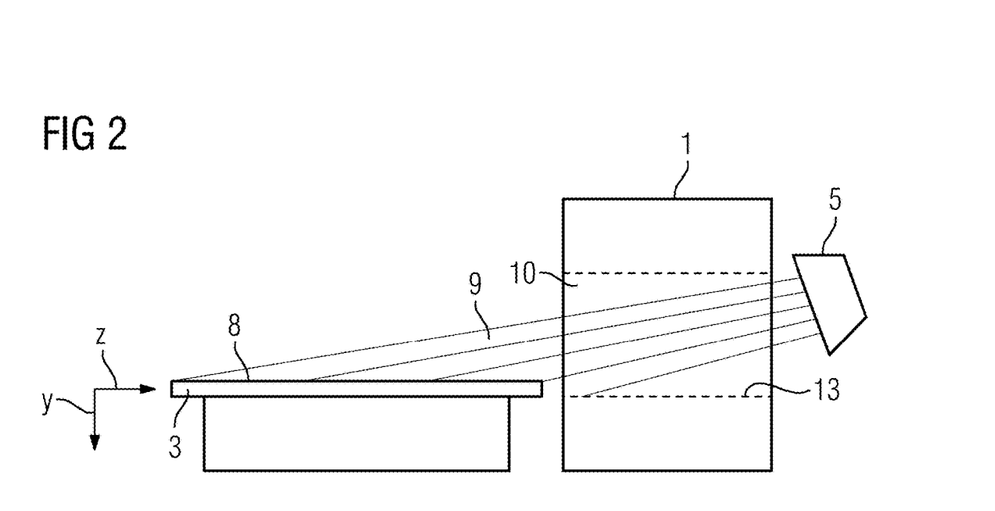
FIG. 2 is a schematic side view of the medical device according to the invention.

FIG. 2 is a schematic side view of an exemplary embodiment of a medical device 1 according to the invention. In this illustration it can be seen that the second light curtain 5 also comprises light barriers spaced a distance apart in the y-direction. For clarity, the first light curtain 4 is not shown. The detection area 9 of the light curtain 5 is extended such that it both at least partially covers the interior of the patient-receiving aperture 10 and also encompasses the area in front of the patient-receiving aperture 10 in which the patient table 3 is disposed for loading the patient. To send back the light emitted by the second light curtain 5, the surface 8 of the patient table 3 has photosensors and/or at least partially reflecting areas. It is additionally or alternatively possible for a third light curtain to be used as part of the light curtain arrangement. The third light curtain is disposed on the side of the medical device 1 opposite the second light curtain 5 and its detection area likewise extends at least partially into the interior of the patient-receiving aperture 10.

Figure 3:
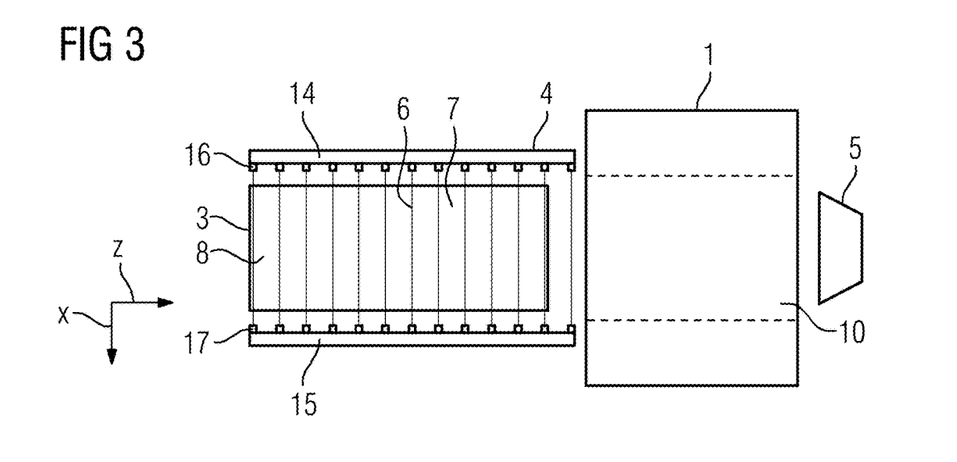
FIG. 3 is schematic view from above of a first exemplary embodiment of the medical device according to the invention.

FIG. 3 is a schematic view of an exemplary embodiment of a medical device 1 according to the invention. The detection area of the second light curtain 5 is not shown for reasons of clarity. The first light curtain 4 has a transmitting section 14 disposed outside the patient-receiving aperture and a reflecting section 15 disposed outside the patient-receiving aperture 10. To form the light barriers 6 covering the detection area 7, the transmitting section 14 has a plurality of light transmitters 16 and the reflecting section 15 has a plurality of light reflectors 17 opposite the light transmitters 16. Instead of light reflectors 17, photosensors can also be used. The detection area 7 of the first light curtain 4 is disposed essentially parallel to a surface 8 of the patient table 3. The light transmitters 16 and the light reflectors 17 can be disposed such that the detection area 7 of the first light curtain 4 also extends in the y-direction, thus enabling the position of a patient 2 positioned on the patient table 3 to be determined in the y-direction and in the z-direction. The second light curtain 5 enables the patient position to be detected in the x-direction and in the y-direction, as shown by way of example in FIGS. 1 and 2. It is alternatively possible for the first light curtain 4, or more specifically the transmitting section 14 and the reflecting section 15, to be implemented such that the detection area 7 of the first light curtain 4 also extends inside the patient-receiving aperture 10.

Figure 4:
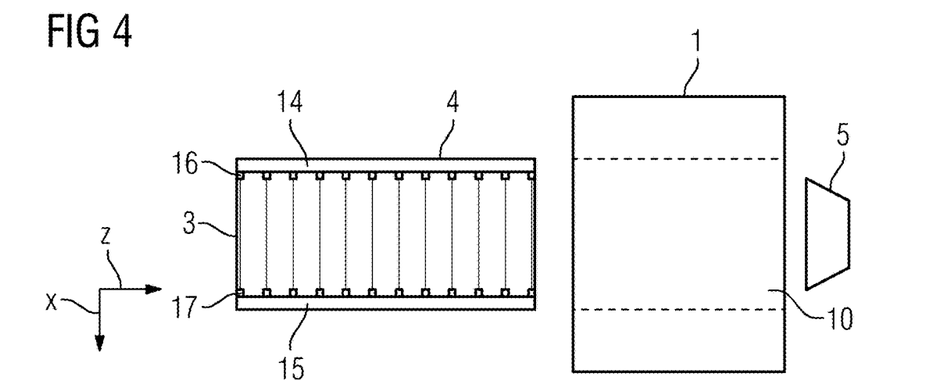
FIG. 4 is a schematic illustration of a second exemplary embodiment of the medical device according to the invention.

FIG. 4 shows a schematic view from above of an alternative embodiment of a medical device 1 according to the invention. For clarity, the detection area 9 of the second light curtain 5 is also not shown in this illustration. In this alternative design, the transmitting section 14 and the reflecting section 15 are disposed on the patient table 3. This enables the position of the patient to be determined even when the patient table 3 is positioned inside the patient-receiving aperture 10.

Figure 5:
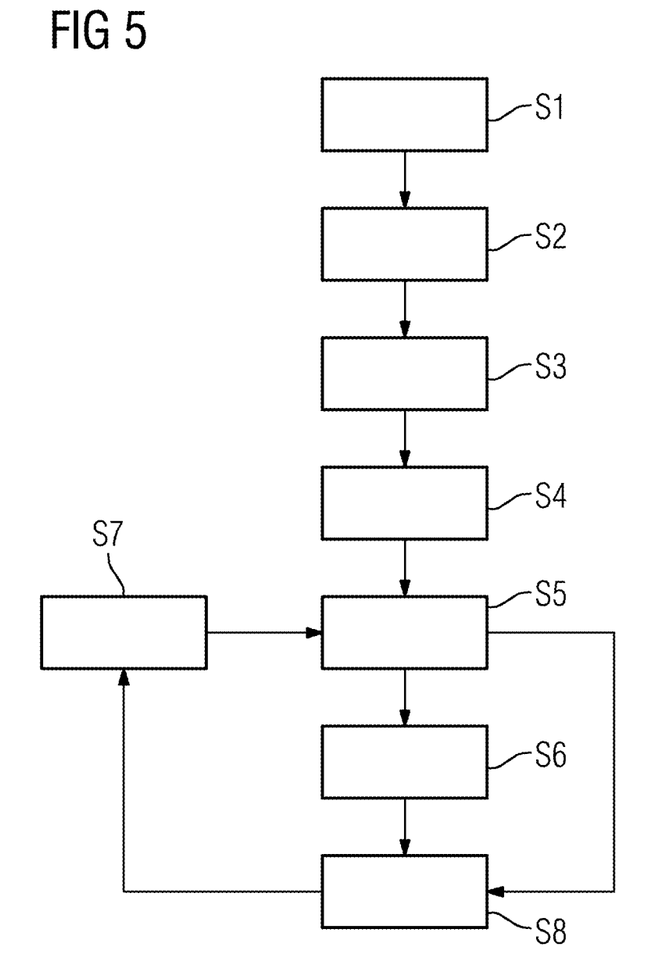
FIG. 5 is a flowchart of the method according to the invention.

FIG. 5 is a flowchart of a method according to the invention. Step S1 represents the start of the method according to the invention. In this step the start position of the patient 2 positioned on the patient table 3 is determined by the three-dimensional light curtain arrangement. In step S2 a position deviation between the start position of the patient and a target position stored in the control processor 11 is then determined by the control processor 11. The target position may have been determined according to the imaging and/or treatment to be carried out by the medical device 1 and according to the position of an accessory unit 12 and stored in the control processor 11. Once the position deviation between start position and target position has been determined, in step S3 the patient table 3 is automatically positioned so that the patient position coincides with the target position. In the subsequent step S4 the imaging and/or treatment to be carried out by the medical device 1 commences.

During the imaging and/or treatment, an instantaneous position of the patient and/or an accessory unit position of the accessory unit 12 is determined in step S5. On the basis of the determined instantaneous position of the patient, in step S6 a position deviation between the instantaneous position of the patient and the target position is determined. If the position deviation determined exceeds a predefined limit value, in step S7 the patient table 3 is automatically re-positioned. Additionally or alternatively, in step 6 an updated target position which is used to determine a position deviation between the instantaneous position of the patient and the updated target position can be determined from an ascertained accessory unit position. Once the patient support or rather the patient has been automatically positioned in step S7, the instantaneous position of the patient and/or the accessory unit position of an accessory unit is re-determined in step S5 for the duration of the imaging and/or treatment to be carried out.

When the imaging and/or treatment by the medical device 1 is complete, the method terminates in step S8. It can be provided that, in step S3 and in step S7, positioning information describing the respective positioning and/or the instantaneous position of the patient and/or the target position is stored in the control processor 11. This is used for documentation of the imaging and/or treatment carried out in order to reproduce the positionings and the instantaneous position of the patient and/or the target position in particular for evaluation of the imaging and/or treatment carried out.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for automatically positioning a patient relative to a medical device, the patient being positioned on a patient support device of the medical device in a detection area of an optical position determining device of the medical device, said optical position determining device comprising a three-dimensional light curtain arrangement that includes a plurality of light curtains, said method comprising:

detecting, with the optical position determining device using said at least one three-dimensional light curtain arrangement, a start position of the patient on the patient support device;

with said light curtain arrangement, producing the plurality of light curtains that each have a respective detection area, with the respective detection areas of said plurality light curtains at least partially intersecting at an angle with respect to each other; and producing a first of said plurality of light curtains so that the detection area thereof is disposed parallel to a surface of the patient support device on which the patient lies, and producing a second of said plurality of light curtains so that the detection area thereof is disposed at an angle to said surface of the patient support device on which the patient lies;

determining, via a control computer using an electronic signal from the optical position determining device that represents the detected position of the patient on the patient support device, a position deviation between said start position and a target position of the patient that is stored in the control computer; and automatically moving, in said control computer using said position deviation, the patient support device three-dimensionally so as to position the patient on the patient support device in said target position.

2. The method as claimed in claim 1, comprising producing said second light curtain of said plurality of light curtains so as to at least partially penetrate a patient-receiving aperture of said medical device.

3. The method as claimed in claim 1, comprising, after said patient support device has been initially three-dimensionally positioned by said control computer, repeatedly detecting respective instantaneous positions of the patient on the patient support device using said optical position determining device during a procedure implemented on the patient by the medical device.

4. The method as claimed in claim 3, comprising storing, in said control computer, at least one procedure target position and, if a procedure position deviation is detected by said control computer between one of the instantaneous positions of the patient and said at least one procedure target position, automatically using said procedure position deviation to control movement of said patient support device from said control computer so as to automatically re-position said patient on said patient support device to said at least one procedure target position.

5. The method as claimed in claim 4, comprising storing a plurality of procedure target positions, which are used in said control computer at different times during the procedure to be implemented on the patient by said medical device for a positioning sequence comprising a plurality of automatic positionings of the patient support device.

6. The method as claimed in claim 1, comprising determining said target position in said control computer using information describing a procedure to be implemented on the patient by said medical device.

7. The method as claimed in claim 1, wherein said medical device comprises an accessory unit that includes at least one sensor, and further comprising:

detecting a position of said accessory unit relative to said medical device;

providing said position of said accessory unit to said control computer; and in said control computer, determining said target position dependent on said position of said accessory unit.

8. The method as claimed in claim 7, wherein an optical position detector of the accessory unit includes at least one light transmitter and/or light receiver to detect said position of said accessory unit; and determining, via said control computer, said position of said accessory unit from said optical position detector.

9. The method as claimed in claim 7, comprising, during a procedure implemented by said medical device on said patient, determining at least one updated target position dependent on the position of the accessory unit;

storing, in the control computer, the at least one updated target position;

detecting an instantaneous position of the patient during said procedure implemented by said medical device;

in said computer, detecting a procedure position deviation between the instantaneous position of the patient and said at least one updated target position; and, automatically repositioning said patient support device in the event of the procedure position deviation between the instantaneous position of the patient and the at least one updated target position.

10. The method as claimed in claim 1, comprising for the automatic moving of the patient support device, storing the position of the patient and the target position.

11. A medical apparatus comprising:

a medical device having a patient support device adapted to receive a patient thereon;

a three-dimensional light curtain arrangement that produces a plurality of light curtains that each have a respective detection area, with the respective detection areas of said plurality light curtains at least partially intersecting at an angle with respect to each other wherein a first of said plurality of light curtains has a respective detection area disposed parallel to a surface of the patient support device on which the patient lies, and wherein a second of said plurality of light curtains has a respective detection area disposed at an angle to said surface of the patient support device on which the patient lies;

an optical position determining device including the three-dimensional light curtain arrangement that uses said plurality of light curtains to detect a start position of the patient on the patient support device;

a control computer provided with an electronic signal from the optical position determining device that represents the detected position of the patient on the patient support device;

said control computer being configured to determine a position deviation between said start position and a target position of the patient that is stored in the control computer; and said control computer being configured to use said position deviation to automatically move the patient support device three-dimensionally so as to position the patient on the patient support device in said target position.

12. A non-transitory, computer-readable data storage medium encoded with programming instructions, said storage medium being loaded into a control computer of a medical device comprising a patient support device adapted to receive a patient thereon, said programming instructions causing said control computer to:

operate a three-dimensional light curtain arrangement so as to produce a plurality of light curtains that each have a respective detection area, with the respective detection areas of said plurality light curtains at least partially intersecting at an angle with respect to each other, a first of said plurality of light curtains having a respective detection area disposed parallel to a surface of the patient support device on which the patient lies, and a second of said plurality of light curtains having a respective detection area disposed at an angle to said surface of the patient support device on which the patient lies;

operate an optical position determining device including the three-dimensional light curtain arrangement to use said plurality of light curtains to detect a start position of the patient on the patient support device;

receive an electronic signal from the optical position determining device that represents the detected position of the patient on the patient support device;

determine a position deviation between said start position and a target position of the patient that is stored in the control computer; and use said position deviation to automatically move the patient support device three-dimensionally so as to position the patient on the patient support device in said target position.

* * * * *